United States Patent
Xu et al.

(10) Patent No.: US 11,547,334 B2
(45) Date of Patent: Jan. 10, 2023

(54) PSYCHOLOGICAL STRESS ESTIMATION METHOD AND APPARATUS

(71) Applicant: Huawei Technologies Co., Ltd., Shenzhen (CN)

(72) Inventors: Peida Xu, Shenzhen (CN); Anqi Zhang, Shenzhen (CN); Yu Zhu, Shenzhen (CN)

(73) Assignee: HUAWEI TECHNOLOGIES CO., LTD., Shenzhen (CN)

( * ) Notice: Subject to any disclaimer, the term of this patent is extended or adjusted under 35 U.S.C. 154(b) by 908 days.

(21) Appl. No.: 16/462,060

(22) PCT Filed: Nov. 17, 2016

(86) PCT No.: PCT/CN2016/106306
§ 371 (c)(1),
(2) Date: May 17, 2019

(87) PCT Pub. No.: WO2018/090304
PCT Pub. Date: May 24, 2018

(65) Prior Publication Data
US 2019/0328301 A1    Oct. 31, 2019

(51) Int. Cl.
*A61B 5/16* (2006.01)
*A61B 5/11* (2006.01)
*A61B 5/145* (2006.01)

(52) U.S. Cl.
CPC .............. *A61B 5/165* (2013.01); *A61B 5/11* (2013.01); *A61B 5/14546* (2013.01); *A61B 2560/0223* (2013.01)

(58) Field of Classification Search
CPC ........ A61B 2560/0223; A61B 5/02416; A61B 5/11; A61B 5/1128; A61B 5/14546;
(Continued)

(56) References Cited

U.S. PATENT DOCUMENTS

2005/0114142 A1    5/2005 Asukai et al.
2012/0289794 A1*  11/2012 Jain ...................... A61B 5/0022
                                                                  600/301
(Continued)

FOREIGN PATENT DOCUMENTS

CN    1626029 A    6/2005
CN    103202699 A    7/2013
(Continued)

OTHER PUBLICATIONS

Machine Translation and Abstract of Chinese Publication No. CN104983434, Oct. 21, 2015, 14 pages.
(Continued)

*Primary Examiner* — Eric J Messersmith
(74) *Attorney, Agent, or Firm* — Conley Rose, P.C.

(57) ABSTRACT

A psychological stress estimation method includes obtaining a physiological signal of a user corresponding to a current moment, determining a first stress indicator of the user based on the current moment and a cyclic stress model of the user, determining a second stress indicator of the user based on the physiological signal of the user corresponding to the current moment and an instantaneous stress model of the user, where the physiological signal is an input of the instantaneous stress model, and determining the current stress indicator of the user based on the first stress indicator and the second stress indicator.

20 Claims, 4 Drawing Sheets

(58) Field of Classification Search
CPC ........ A61B 5/165; A61B 5/318; G16H 10/20; G16H 10/40; G16H 40/63; G16H 50/50
See application file for complete search history.

(56) References Cited

U.S. PATENT DOCUMENTS

| | | | |
|---|---|---|---|
| 2014/0288401 A1 | 9/2014 | Ouwerkerk et al. | |
| 2015/0120205 A1 | 4/2015 | Jeon et al. | |
| 2017/0127993 A1* | 5/2017 | Olivier | A61B 5/4227 |
| 2018/0303396 A1* | 10/2018 | Wild | G16H 50/70 |

FOREIGN PATENT DOCUMENTS

| | | |
|---|---|---|
| CN | 103957783 A | 7/2014 |
| CN | 104239288 A | 12/2014 |
| CN | 104490407 A | 4/2015 |
| CN | 104688249 A | 6/2015 |
| CN | 104983434 A | 10/2015 |
| CN | 105193431 A | 12/2015 |
| CN | 105232063 A | 1/2016 |
| CN | 105559803 A | 5/2016 |
| CN | 105679333 A | 6/2016 |
| CN | 106037764 A | 10/2016 |
| JP | H1119076 A | 1/1999 |
| JP | H1138004 A | 2/1999 |
| JP | 2000126143 A | 5/2000 |
| JP | 2001204696 A | 7/2001 |
| JP | 5328030 B2 | 10/2013 |
| RU | 2299681 C1 | 5/2007 |

OTHER PUBLICATIONS

Machine Translation and Abstract of Chinese Publication No. CN105193431, Dec. 30, 2015, 16 pages.
Machine Translation and Abstract of Chinese Publication No. CN105679333, Jun. 15, 2016, 17 pages.
Machine Translation and Abstract of Chinese Publication No. CN106037764, Oct. 26, 2016, 22 pages.
Machine Translation and Abstract of Japanese Publication No. JP5328030, Oct. 30, 2013, 37 pages.
Machine Translation and Abstract of Japanese Publication No. JP2000126143, May 9, 2000, 7 pages.
Machine Translation and Abstract of Japanese Publication No. JPH1119076, Jan. 26, 1999, 7 pages.
Machine Translation and Abstract of Japanese Publication No. JPH1138004, Feb. 12, 1999, 6 pages.
Machine Translation and Abstract of Russian Publication No. RU2299681, May 27, 2007, 7 pages.
Foreign Communication From a Counterpart Application, Chinese Application No. 201680080732.3, Chinese Office Action dated Oct. 9, 2019, 6 pages.
Machine Translation and Abstract of Chinese Publication No. CN103202699, Jul. 17, 2013, 5 pages.
Machine Translation and Abstract of Chinese Publication No. CN104239288, Dec. 24, 2014, 19 pages.
Machine Translation and Abstract of Chinese Publication No. CN104490407, Apr. 8, 2015, 9 pages.
Machine Translation and Abstract of Chinese Publication No. CN104688249, Jun. 10, 2015, 9 pages.
Machine Translation and Abstract of Chinese Publication No. CN105232063, Jan. 13, 2016, 15 pages.
Machine Translation and Abstract of Chinese Publication No. CN105559803, May 11, 2016, 20 pages.
Foreign Communication From a Counterpart Application, PCT Application No. PCT/CN2016/106306, English Translation of International Search Report dated Aug. 29, 2017, 2 pages.
Foreign Communication From a Counterpart Application, PCT Application No. PCT/CN2016/106306, English Translation of Written Opinion dated Aug. 29, 2017, 4 pages.
Machine Translation and Abstract of Japanese Publication No. JP2001204696, Jul. 31, 2001, 14 pages.

* cited by examiner

PSYCHOLOGICAL STRESS ESTIMATION METHOD AND APPARATUS

CROSS-REFERENCE TO RELATED APPLICATIONS

This application is a U.S. National Stage of International Patent Application No, PCT/CN2016/106306 filed Nov. 17, 2016, which is hereby incorporated by reference in its entirety.

TECHNICAL FIELD

The present invention relates to the field of psychological health application technologies, and in particular, to a psychological stress estimation method and apparatus.

BACKGROUND

With popularity of wearable devices, more and more wearable devices can collect people's physiological parameters in a daily scenario, for example, a heart rate and a skin temperature. Statistics collection and prediction on people's physiological health statuses can be more effectively performed through long-term collection of physiological data. In addition to physiological health, people's psychological health problem cannot be ignored either. A psychological health problem is caused mainly due to a relatively large psychological stress. Development of wearable devices provides a new carrier for psychological stress estimation.

Currently, a stress level or a stress value of a user may be obtained in the following manners: subjectively providing the stress value or the stress level by the user; determining the stress value or the stress level of the user by performing psychological statistical analysis on a result of a stress questionnaire filled in by the user; determining the stress value or the stress level of the user based on a cortisol level of the user; and determining the stress value or the stress level of the user based on a text record, an expression, an action, a motion status, or audio of the user. However, the stress value or the stress level of the user cannot be obtained at any time and at any place in these manners.

In addition, there is a manner of performing modeling on a bioelectric signal of the user to obtain an instantaneous stress model of the user, and determining the stress value or the stress level based on the instantaneous stress model of the user. However, determining the stress value or the stress level of the user based only on the bioelectric signal of the user leads to low accuracy. In addition, the bioelectric signal of the user is prone to be affected by an instantaneous factor (such as a sudden emotional change, a temperature, and light). As a result, the instantaneous stress model of the user is prone to be affected by the instantaneous factor and has weak robustness.

SUMMARY

Embodiments of the present invention provide a psychological stress estimation method and apparatus, to improve accuracy of a psychological stress estimation result of a user and improve robustness of a system for estimating a user psychological stress.

To achieve the foregoing objective, the following technical solutions are used in the embodiments of the present invention.

According to a first aspect, a psychological stress estimation method is provided, and the method includes: obtaining a physiological signal of a user corresponding to a current moment; determining a first stress indicator of the user based on the current moment and a cyclic stress model of the user, where the cyclic stress model is a stress model that is determined based on stress indicators of the user corresponding to a plurality of moments and that can be used to determine a current stress indicator of the user based only on the current moment; determining a second stress indicator of the user based on the physiological signal of the user corresponding to the current moment and an instantaneous stress model of the user, where the instantaneous stress model is a stress model that is used to determine a current stress indicator of the user based on a physiological signal related to a current stress status of the user, and the physiological signal is input of the instantaneous stress model; and determining the current stress indicator of the user based on the first stress indicator and the second stress indicator; or the method includes: obtaining a physiological signal of a user corresponding to a current moment; and determining a stress indicator of the user based on the current moment, the physiological signal of the user corresponding to the current moment, and a target stress model, where the target stress model is a stress model that is determined by comprehensively processing a cyclic stress model and an instantaneous stress model, the cyclic stress model is a stress model that is determined based on stress indicators of the user corresponding to a plurality of moments and that can be used to determine a current stress indicator of the user based only on the current moment, the instantaneous stress model is a stress model that is used to determine a current stress indicator of the user based on a physiological signal related to a current stress status of the user, and the physiological signal is input of the instantaneous stress model.

According to the method provided in the first aspect, the current stress indicator of the user is determined based on the cyclic stress model and the instantaneous stress model. The cyclic stress model is a stress model that is determined based on stress indicators of the user corresponding to a plurality of moments and that can be used to determine a current stress indicator of the user based only on the current moment. Therefore, the cyclic stress model may mainly reflect a stress indicator of the user in a time period and is not prone to be affected by an instantaneous factor, ensuring robustness of a psychological stress estimation system. In addition, the instantaneous stress model is a stress model that needs to be used to determine a current stress indicator of the user based on a physiological signal related to a current stress status of the user, so that the psychological stress estimation system also determines the current stress indicator of the user based on the current stress status of the user, and accuracy of the psychological stress estimation system is improved.

In a possible design, the cyclic stress model is a stress model that is determined based on at least one type of discrete stress indicator set, the discrete stress indicator set is a set of stress indicators that are determined based on discrete stress data that is obtained in a preset time period and is corresponding to at least one time point, and a discrete stress indicator in the discrete stress indicator set is a stress indicator that is determined based on a subjective estimation result of the user, a cortisol level of the user, or an external behavior of the user.

In a possible design, the cyclic stress model includes a subjective cyclic stress model and an objective cyclic stress model; the subjective cyclic stress model is a stress model that is determined based on a type-1 discrete stress indicator set and/or a type-2 discrete stress indicator set, a discrete stress indicator in the type-1 discrete stress indicator set is a stress indicator that is determined based on a subjective estimation result of the user, and a discrete stress indicator in the type-2 discrete stress indicator set is a stress indicator that is determined based on an external behavior of the user; the objective cyclic stress model is a stress model that is determined based on a type-3 discrete stress indicator set, and a discrete stress indicator in the type-3 discrete stress indicator set is a stress indicator that is determined based on a cortisol level of the user; and the discrete stress indicator set is a set of stress indicators that are determined based on discrete stress data that is obtained in a preset time period and is corresponding to at least one time point.

In a possible design, the cyclic stress model is a stress model that is determined based on a comprehensive discrete stress indicator set, the comprehensive discrete stress indicator set is a set of stress indicators that are determined based on at least one type of discrete stress indicator set, a comprehensive discrete stress indicator in the comprehensive discrete stress indicator set is determined based on a plurality of discrete stress indicators, the plurality of discrete stress indicators are all discrete stress indicators corresponding to a same time point in the at least one type of discrete stress indicator set, the discrete stress indicator set is a set of stress indicators that are determined based on discrete stress data that is obtained in a preset time period and is corresponding to at least one time point, and a discrete stress indicator in the discrete stress indicator set is a stress indicator that is determined based on a subjective estimation result of the user, a cortisol level of the user, or an external behavior of the user.

In a possible design, the cyclic stress model is a stress model that is determined based on a comprehensive discrete stress indicator set and a plurality of historical discrete stress indicators, the comprehensive discrete stress indicator set is a set of stress indicators that are determined based on at least one type of discrete stress indicator set, a comprehensive discrete stress indicator in the comprehensive discrete stress indicator set is determined based on a plurality of discrete stress indicators, the plurality of discrete stress indicators are all discrete stress indicators corresponding to a same time point in the at least one type of discrete stress indicator set, the discrete stress indicator set is a set of stress indicators that are determined based on discrete stress data that is obtained in a preset time period and is corresponding to at least one time point, and a discrete stress indicator in the discrete stress indicator set is a stress indicator that is determined based on a subjective estimation result of the user, a cortisol level of the user, or an external behavior of the user; and the historical discrete stress indicator is a discrete stress indicator that is obtained before the preset time period.

In this possible design, the determined cyclic stress model can be more accurate by using the historical discrete stress indicator.

In this possible design, before the determining a second stress indicator of the user based on the current physiological signal and an instantaneous stress model of the user, the method further includes: obtaining M physiological signals of the user in M time periods, where a physiological signal segment is a physiological signal of the user obtained in a time period, and M is an integer greater than 0; obtaining stress indicators that are subjectively provided by the user in M time periods, to obtain M subjective stress indicators, where the M subjective stress indicators are corresponding to the M time periods, respectively, and the M time periods are M time periods in which the M physiological signal segments are obtained; using the M physiological signal segments as input of a general stress model to obtain M general stress indicators; subtracting the M general stress indicators from the M subjective stress indicators to obtain M user offsets, where subtraction is performed between a subjective stress indicator and a general stress indicator that are corresponding to a same time period of the M time periods; and determining a sum of an average value of the M user offsets and a result of the general stress model as the instantaneous stress model.

In this possible design, before the determining a second stress indicator of the user based on the current physiological signal and an instantaneous stress model of the user, the method further includes: obtaining a user offset, where the user offset is an offset, stored in another device and associated with the user, used to calibrate a general stress model; and determining a sum of the user offset and a result of the general stress model as the instantaneous stress model of the user.

In this possible design, the physiological signal is a motion signal and/or a bioelectric signal.

According to a second aspect, a psychological stress estimation apparatus is provided, where the psychological stress estimation apparatus has functions of implementing any method according to the first aspect. The functions may be implemented by using hardware or by executing corresponding software by hardware. The hardware or software includes one or more units corresponding to the functions.

According to a third aspect, a psychological stress estimation apparatus is provided, including a processor, a memory, a bus, and a communications interface, where the memory is configured to store a computer executable instruction, the processor is connected to the memory by using the bus, and the processor executes the computer executable instruction stored in the memory, to perform any method according to the first aspect.

For technical effects brought by any design manner in the second and third aspects, refer to technical effects brought by different design manners in the first aspect. Details are not repeated herein.

DESCRIPTION OF EMBODIMENTS

Figure 1:
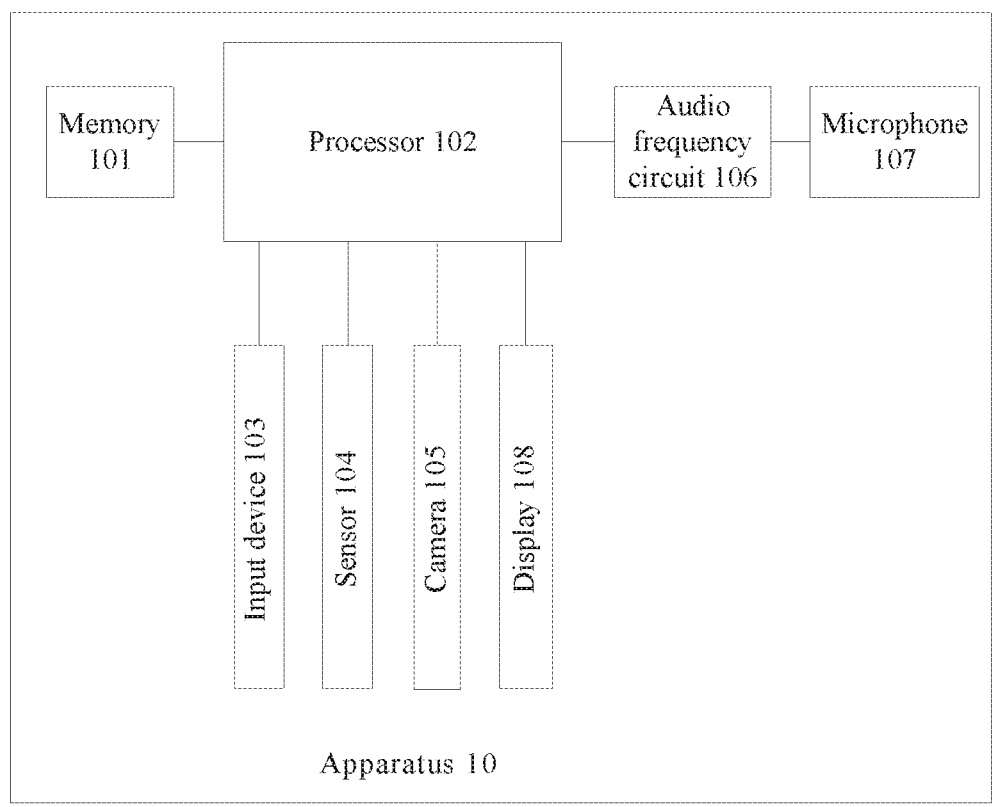
FIG. 1 is a schematic diagram of composition of an apparatus configured to implement a method provided in an embodiment of the present invention according to an embodiment of the present invention.

The term "and/or" in this specification describes only an association relationship for describing associated objects and represents that three relationships may exist. For example, A and/or B may represent the following three cases: Only A exists, both A and B exist, and only B exists. The term "a plurality of" in this specification means two or more than two.

Cortisol, referred to as a corticosteroid hormone, is a hormone that can be naturally produced by a human body. When being exposed to significant stresses, a human being produces more of such a hormone. Therefore, cortisol is also referred to as a stress hormone. Cortisol measurement is a gold standard for current psychological stress measurement. During stress measurement performed by using cortisol, it is found that cortisol itself is affected by a biological clock. This indicates that a stress of a user is not only affected by some instantaneous factors (such as an emotional change, a temperature, and light), but also related to time. Therefore, the embodiments of the present invention provide a psychological stress estimation method in which estimation results of an instantaneous psychological stress and a cyclic psychological stress are comprehensively utilized, to improve robustness and accuracy of a psychological stress estimation system.

In a process of performing the method provided in the embodiments of the present invention, a stress indicator of a user needs to be obtained, and the stress indicator may be a stress value or a stress level. Various manners for obtaining the stress indicator are briefly described below.

Manner 1. The user subjectively provides the stress indicator. Specifically, in this manner, the user subjectively estimates a current stress status of the user and provides the stress indicator.

Manner 2. The stress indicator of the user is determined based on a result of a stress questionnaire filled in by the user. This manner is specifically as follows: The user fills in the stress questionnaire, and an apparatus (or another person) for determining a stress indicator may determine, based on the result of the stress questionnaire filled in by the user, the stress indicator of the user according to a preset rule (or by performing psychological statistical analysis).

Manner 3. The stress indicator of the user is determined based on a cortisol level of blood of the user. In this manner, the blood of the user needs to be drawn, and a higher cortisol level of the blood indicates a higher stress indicator of the user.

Manner 4. The stress indicator of the user is determined based on a text record of the user. The text record in this manner may be a text record on a social networking site or a daily essay of the user. For example, some keyword groups including keywords may be preset, and different keyword groups are corresponding to different stress indicators. Matching the text record with the keyword groups is performed, and a stress indicator is determined based on a matching result.

Manner 5. The stress indicator of the user is determined based on a video of the user. Specifically, the stress indicator of the user may be determined based on an expression, an action, or a voice of the user in the video. For example, some expressions may be preset, and different expressions are corresponding to different stress indicators. Matching the expression of the user in the video with the preset expressions is performed, to determine the stress indicator.

Manner 6. The stress indicator of the user is determined based on audio of the user. Specifically, the stress indicator of the user may be determined based on a tone, a speaking speed, or the like of the user.

In addition, there are other methods for obtaining the stress indicator, and the other methods are not described one by one herein.

In the process of performing the method provided in the embodiments of the present invention, a physiological signal of the user further needs to be obtained, and the physiological signal may be a motion signal and/or a bioelectric signal. Specifically, the motion signal of the user may be obtained by using a motion sensor. The bioelectric signal may be specifically an electrocardiogram (electrocardiogram, ECG for short) signal and/or a photoplethysmograph (photoplethysmograph, PPG for short) signal. Specifically, a bioelectric signal of the user in a time period may be collected by using a wearable device. For example, a PPG signal may be obtained by using a smartwatch.

To make the technical solutions in the embodiments of the present invention clearer, related terms mentioned in the embodiments of the present invention are briefly described first:

Discrete stress indicator: The discrete stress indicator is a stress indicator that is obtained based on discrete stress data of a user, and the discrete stress data is discrete instead of continuous in time.

Comprehensive discrete stress indicator: The comprehensive discrete stress indicator is a stress indicator determined based on a plurality of discrete stress indicators that are obtained at a same time point.

Subjective stress indicator: The subjective stress indicator is a stress indicator determined based on a stress indicator that is subjectively provided by a user in a time period.

General stress indicator: The general stress indicator is a stress indicator that is obtained by using a physiological signal segment as input of a general stress model.

First stress indicator: The first stress indicator is a user stress indicator that is determined based on a current moment and a cyclic stress model of a user.

Second stress indicator: The second stress indicator is a user stress indicator that is determined based on a physiological signal of a user corresponding to a current moment and an instantaneous stress model of the user.

Referring to FIG. 1, an embodiment of the present invention provides an apparatus 10 to implement the method provided in the embodiments of the present invention. The apparatus 10 includes at least a memory 101 and a processor 102 connected to the memory 101. The memory 101 may be configured to store data and a software program. The processor 102 may perform data processing by running the software program. The processor 102 may be a central processing unit (Central Processing Unit, CPU for short), a general processor, a digital signal processor (Digital Signal Processor, DSP for short), an application-specific integrated circuit (Application Specific Integrated Circuit, ASIC for short), a field programmable gate array (Field Programmable Gate Array, FPGA for short) or another programmable logic device, a transistor logic device, a hardware component, or any combination thereof. The memory 101 may include a read only memory (Read Only Memory, ROM for short), a random access memory (Random Access Memory, RAM for short), another type of dynamic memory device that can store information and an instruction, or a magnetic disk memory.

The apparatus 10 may further include: an input device 103 connected to the processor 102, where the input device 103 may be configured to input a stress indicator into the apparatus 10; a sensor 104 connected to the processor 102, where the sensor 104 may be configured to obtain a motion signal or a bioelectric signal; a camera 105 connected to the processor 102, where the camera 105 may be configured to collect video data of a user; an audio frequency circuit 106 connected to the processor 102; a microphone 107 connected to the audio frequency circuit 106, where the microphone 107 may provide an audio interface between the user and the apparatus 10 and convert a collected voice signal of the user into an electrical signal, and the audio frequency circuit 106 receives the electrical signal and converts the electrical signal into audio data; and a display 108 connected to the processor 102, where the display 108 is configured to display a finally-obtained stress indicator of the user or display the input stress indicator for the user.

Figure 2:
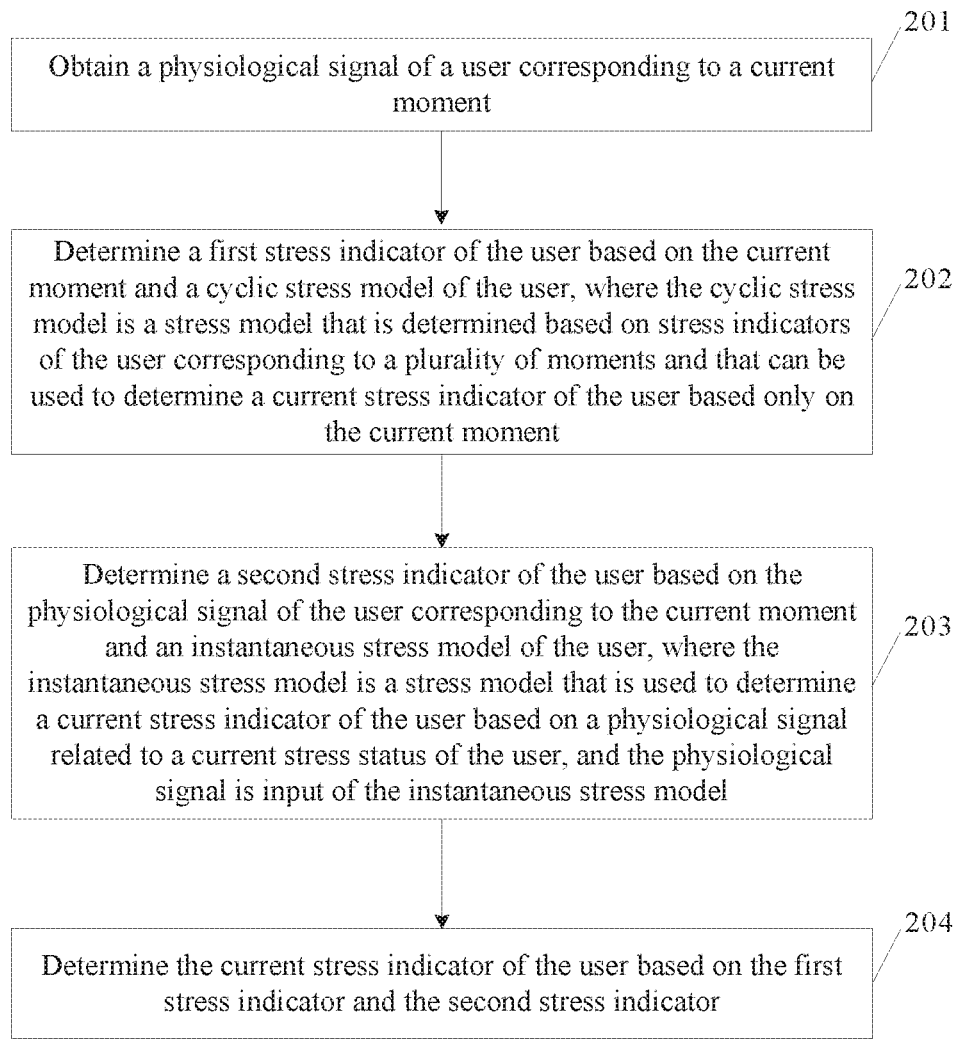
FIG. 2 is a flowchart of a psychological stress estimation method according to an embodiment of the present invention.

An embodiment of the present invention provides a psychological stress estimation method. As shown in FIG. 2, the method includes the following steps.

201. Obtain a physiological signal of a user corresponding to a current moment.

This embodiment of the present invention may be executed by a device having a data computing and processing function, for example, a computer and a wearable device (such as a smartwatch). Step 201 to step 204 may be specifically performed by the processor 102 of the apparatus 10.

202. Determine a first stress indicator of the user based on the current moment and a cyclic stress model of the user, where the cyclic stress model is a stress model that is determined based on stress indicators of the user corresponding to a plurality of moments and that can be used to determine a current stress indicator of the user based only on the current moment.

203. Determine a second stress indicator of the user based on the physiological signal of the user corresponding to the current moment and an instantaneous stress model of the user, where the instantaneous stress model is a stress model that is used to determine a current stress indicator of the user based on a physiological signal related to a current stress status of the user, and the physiological signal is input of the instantaneous stress model.

Optionally, the physiological signal may be a motion signal and/or a bioelectric signal.

The cyclic stress model and the instantaneous stress model may be pre-stored in a device that performs the method.

204. Determine the current stress indicator of the user based on the first stress indicator and the second stress indicator.

In this case, a first stress indicator of the user corresponding to a moment may be determined based on the cyclic stress model, and a second stress indicator of the user corresponding to the moment may be determined based on the instantaneous stress model. These two stress indicators are comprehensively processed to obtain a stress indicator of the user corresponding to the moment. For example, the stress indicator of the user corresponding to the moment is determined by performing weighted summation or performing averaging on the first stress indicator and the second stress indicator.

In another implementable manner, a device that performs the method may pre-store a target stress model. The target stress model is a stress model that is determined by comprehensively processing a cyclic stress model and an instantaneous stress model. In this case, in specific implementation, the method may include: obtaining a physiological signal of a user corresponding to the current moment, and determining a stress indicator of the user based on the current moment, the physiological signal of the user corresponding to the current moment, and the target stress model.

The target stress model may be specifically a stress model that is determined by comprehensively processing the cyclic stress model and the instantaneous stress model in a weighted summation manner, a weighted geometric averaging manner, a weighted harmonic averaging manner, or the like. For example, if a weighted summation manner is used to determine the target stress model, the cyclic stress model is denoted as $Y\_cycle$, and the instantaneous stress model is denoted as $Y\_instant$, the target stress model is $Y\_final = p \cdot Y\_cycle + q \cdot Y\_instant$, where $p+q=1$, for example, $p=0.8$ and $q=0.2$.

According to the method provided in this embodiment of the present invention, the current stress indicator of the user is determined based on the cyclic stress model and the instantaneous stress model. The cyclic stress model is a stress model that is determined based on stress indicators of the user corresponding to a plurality of moments and that can be used to determine a current stress indicator of the user based only on the current moment. Therefore, the cyclic stress model may mainly reflect a stress indicator of the user in a time period and is not prone to be affected by an instantaneous factor, ensuring robustness of a psychological stress estimation system. In addition, the instantaneous stress model is a stress model that needs to be used to determine a current stress indicator of the user based on a physiological signal related to a current stress status of the user, so that the psychological stress estimation system also determines the current stress indicator of the user based on the current stress status of the user, and accuracy of the psychological stress estimation system is improved.

Specifically, the cyclic stress model may be a stress model that is determined in any of the following manners.

Manner 1. A stress model is determined based on at least one type of discrete stress indicator set.

The discrete stress indicator set may be a set of stress indicators that are determined based on discrete stress data that is obtained in a preset time period and is corresponding to at least one time point. A discrete stress indicator in the discrete stress indicator set is a stress indicator that is determined based on a subjective estimation result of the user, a cortisol level of the user, or an external behavior of the user.

The stress indicator determined based on the subjective estimation result of the user may be specifically a stress indicator that is provided after the user subjectively estimates a current stress status of the user, where the discrete stress data may be the stress indicator, or a stress indicator of the user that is determined based on a result of a stress questionnaire filled in by the user, where the discrete stress data may be the result of the stress questionnaire filled in by the user. The stress indicator determined based on the external behavior of the user may be specifically a stress indicator of the user that is determined based on a text record, an expression, an action, a voice, or audio of the user, where the discrete stress data may be the text record, the expression, the action, the voice, or the audio of the user. The discrete stress indicators that are obtained in these manners are not prone to be affected by an instantaneous factor such as a sudden emotion change, a temperature, or light and therefore are relatively reliable, but have relatively poor portability. Therefore, the discrete stress indicators may be used to determine the cyclic stress model of the user, so that the cyclic stress model is not prone to be affected by an instantaneous factor.

Specifically, one discrete stress indicator may be corresponding to one time point, and the time point corresponding to the discrete stress indicator is a time point at which data for determining the discrete stress indicator is obtained. The preset time period may be any time period. For example, the preset time period may be one day, one week, a workday of one week, or the like. The stress indicator may be a stress value or a stress level. A higher stress value or stress level indicates a higher psychological stress of the user.

For example, it is assumed that there are three types of discrete stress indicators. As shown in Table 1, T0 to T9 are 10 time points in a preset time period. Table 1 lists discrete stress indicators in type-1, type-2, and type-3 discrete stress indicator sets. Discrete stress indicators in the type-1 discrete stress indicator set are stress indicators that are determined based on a subjective estimation result of the user, and specifically include S10, S11, S14. S15, S17, and S19. These six discrete stress indicators are corresponding to time points T0, T1, T4, T5, T7, and T9, respectively. Discrete stress indicators in the type-2 discrete stress indicator set are stress indicators that are determined based on an external behavior of the user, and specifically include S20, S22, S23, S24, S25, S26, and S28. These six discrete stress indicators are corresponding to time points T0, T2, T3, T4, T5, T6, and T8, respectively. Discrete stress indicators in the type-3 discrete stress indicator set are stress indicators that are determined based on a cortisol level of the user, and specifically include S30, S31, S33, S34, S36, S37, and S39. These seven discrete stress indicators are corresponding to time points T0, T1, T3, T4, T6. T7, and T9, respectively.

are corresponding to a same time point. When only one discrete stress indicator is obtained at a time point, the discrete stress indicator is a comprehensive discrete stress indicator corresponding to the time point. When a plurality of discrete stress indicators are obtained at a time point and the plurality of discrete stress indicators are discrete stress indicators that are obtained in different obtaining manners, a comprehensive discrete stress indicator corresponding to the time point may be a stress indicator that is obtained by performing averaging on the plurality of discrete stress indicators corresponding to the time point, or may be a stress indicator that is determined by assigning different weights to the plurality of discrete stress indicators obtained at the time point and then performing weighted summation.

For example, based on the example shown in FIG. 1, 10 comprehensive discrete stress indicators may be determined, a comprehensive discrete stress indicator corresponding to T0 may be (S10+S20+S30)/3, and a comprehensive discrete stress indicator corresponding to T2 may be S22.

Specifically, the cyclic stress model may be obtained by performing curve fitting on the comprehensive discrete stress indicators in the comprehensive discrete stress indicator set by using a cubic spline interpolation algorithm or a polynomial fitting method.

Figure 3:
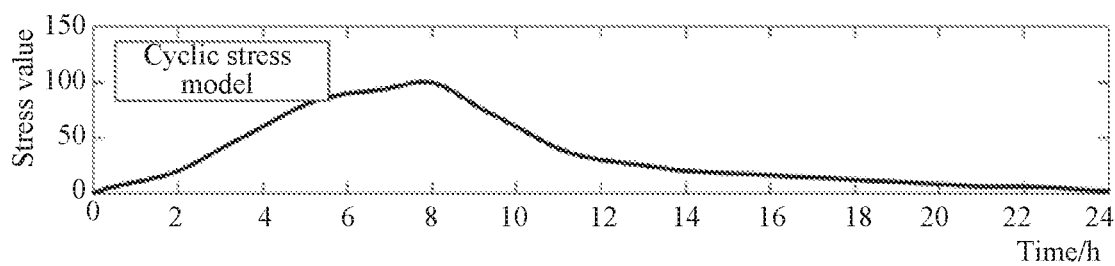
FIG. 3 is a schematic diagram of a cyclic stress model according to an embodiment of the present invention.

For example, as shown in FIG. 3, FIG. 3 shows a cyclic stress model that is obtained through fitting.

TABLE 1

| Type of a discrete stress indicator set | T0 | T1 | T2 | T3 | T4 | T5 | T6 | T7 | T8 | T9 |
|---|---|---|---|---|---|---|---|---|---|---|
| Type 1 | S10 | S11 | | | S14 | S15 | | S17 | | S19 |
| Type 2 | S20 | | S22 | S23 | S24 | S25 | S26 | | S28 | |
| Type 3 | S30 | S31 | | S33 | S34 | | S36 | S37 | | S39 |

It should be noted that, the discrete stress indicators in the type-1 discrete stress indicator set may be a set of stress indicators that are provided based on subjective estimation performed by the user on a current stress status of the user, or may be a set of user stress indicators that are determined based on a result of a stress questionnaire filled in by the user. Alternatively, the type-1 discrete stress indicator set may include a set of stress indicators that are provided based on subjective estimation performed by the user on a current stress status of the user and a set of user stress indicators that are determined based on a result of a stress questionnaire filled in by the user. Other discrete stress indicator sets are similar to the type-1 discrete stress indicator set.

Specifically, the cyclic stress model may be obtained by performing curve fitting on the discrete stress indicators in the discrete stress indicator set by using a cubic spline interpolation algorithm or a polynomial fitting method.

Manner 2. A stress model is determined based on a comprehensive discrete stress indicator set.

The comprehensive discrete stress indicator set may be a set of stress indicators that are determined based on at least one type of discrete stress indicator set. A comprehensive discrete stress indicator in the comprehensive discrete stress indicator set is determined based on a plurality of discrete stress indicators, and the plurality of discrete stress indicators are all discrete stress indicators corresponding to a same time point in the at least one type of discrete stress indicator set.

A comprehensive discrete stress indicator may be determined based on a plurality of discrete stress indicators that Manner 3. A stress model is determined based on a comprehensive discrete stress indicator set and a plurality of historical discrete stress indicators, where the historical discrete stress indicator is a discrete stress indicator that is obtained before a preset time period.

Specifically, when the preset time period is one day, the historical discrete stress indicator may be a discrete stress indicator that is obtained one or more days before a date corresponding to the preset time period. When the preset time period is a day within one week, for example, when the preset time period is Monday, the historical discrete stress indicator may be a discrete stress indicator that is obtained on Monday in one or more weeks before a date corresponding to the preset time period. Alternatively, the historical discrete stress indicator may be a discrete stress indicator that is obtained at another time. Only an example is used for description herein.

In this case, modeling can be performed by using a one-dimensional quadratic function. To be specific, the cyclic stress model=$ax^2+bx+c$, where x is a time point, and a, b, and c are constants, and the coefficient terms a, b, c is determined by using an optimum method. During calculation of a total error of all discrete stress indicators, an error weight of a discrete stress indicator obtained in a preset time period is 1, and an error weight of a historical discrete stress indicator is less than 1. To be specific, when a discrete stress indicator in historical discrete stress indicators is obtained at a time point closer to the preset time period, an error weight of the discrete stress indicator is closer to 1, so that a discrete stress indicator obtained more recently has greater impact on an optimization result; otherwise, a discrete stress indicator obtained earlier has smaller impact on the optimization result. This makes the determined cyclic stress model more accurate.

Optionally, the cyclic stress model may include a subjective cyclic stress model and an objective cyclic stress model. The subjective cyclic stress model is a stress model that is determined based on the type-1 discrete stress indicator set and/or the type-2 discrete stress indicator set. The objective cyclic stress model is a stress model that is determined based on the type-3 discrete stress indicator set.

For concepts of the type-1 discrete stress indicator set, the type-2 discrete stress indicator set, the type-3 discrete stress indicator set, and the discrete stress indicator set, refer to the foregoing description.

Specifically, when the discrete stress indicator set used to determine the objective cyclic stress model includes a total of N1 discrete stress indicators and one or more discrete stress indicator sets used to determine the subjective cyclic stress model include a total of N2 discrete stress indicators, N1' comprehensive discrete stress indicators may be determined based on the N1 discrete stress indicators, N2' comprehensive discrete stress indicators may be determined based on the N2 discrete stress indicators, the objective cyclic stress model may be determined based on the N1' comprehensive discrete stress indicators, and the subjective cyclic stress model may be determined based on the N2' comprehensive discrete stress indicators. The N1' comprehensive discrete stress indicators are corresponding to N1' time points, respectively, and a comprehensive discrete stress indicator corresponding to a time point is determined based on a discrete stress indicator that is obtained at the time point and that is of the N1 discrete stress indicators. The N2' comprehensive discrete stress indicators are corresponding to N2' time points, respectively, and a comprehensive discrete stress indicator corresponding to a time point is determined based on a discrete stress indicator that is obtained at the time point and that is of the N2 discrete stress indicators.

For example, the N1 discrete stress indicators may be cortisol levels of the user that are obtained at N1 fixed moments within a preset time period. The objective cyclic stress model may be obtained by performing curve fitting on the N1 discrete stress indicators. For example, if the preset time period is one day and N1=5, the N time points at which the N1 discrete stress indicators are obtained may be 8 o'clock, 10 o'clock, 14 o'clock, 16 o'clock, and 20 o'clock. When the stress indicator is a stress value, a highest one of cortisol levels measured at the N1 time points may be corresponding to a stress value 100, and a lowest one of the cortisol levels may be corresponding to a stress value 0. A higher cortisol level indicates a greater stress value, so that all the discrete stress indicators corresponding to the N time points may be determined.

Based on this optional method, the target stress model may be specifically a stress model that is determined by comprehensively processing the objective cyclic stress model, the subjective cyclic stress model, and the instantaneous stress model in a weighted summation manner, a weighted geometric averaging manner, a weighted harmonic averaging manner, or the like. For example, if the weighted summation manner is used, the subjective cyclic stress model is denoted as Y_subject, the objective cyclic stress model is denoted as Y_object, and the instantaneous stress model is denoted as Y_instant, the target stress model is $Y\_final = p1 \cdot Y\_subject + p2 \cdot Y\_object + q \cdot Y\_instant$, where $p1+p2+q=1$, for example, $p1=0.5$, $p2=0.3$, and $q=0.2$.

Optionally, the instantaneous stress model of the user may be a general stress model.

A method for establishing a general stress model specifically includes: determining, as samples, a preset quantity of individuals that are within a same age range as the user; obtaining sample information of each individual, where the sample information of the individual includes basic information (a gender, an age, a height, a weight, and the like of the individual) of the individual, a physiological signal of the individual within a time period, and a stress indicator subjectively provided by the individual; determining a feature vector of the individual, where a method for determining the feature vector of the individual may specifically include extracting a feature of the physiological signal of the individual within the time period, and forming the feature vector by using the extracted feature and the basic information of the individual; constructing a linear regression equation of the individual, where a method for constructing the linear regression equation of the individual may include constructing the linear regression equation based on the feature vector of the individual and the stress indicator subjectively provided by the individual, where the stress indicator subjectively provided by the individual is output of the equation; constructing a linear regression equation set based on linear regression equations of the preset quantity of individuals; obtaining a regression coefficient of the linear regression equation set through calculation by using a least square method; and using each parameter of the feature vector as an independent variable, using a regression coefficient corresponding to each independent variable as a coefficient of the independent variable, and using the stress indicator as a dependent variable, to obtain the general stress model.

For example, 50 men and 50 women aged from 20 years old to 30 years old are determined, to record basic information of each person. The basic information may include a gender, an age, a height, and a weight. An ECG signal of the person within one minute is collected, and the person is asked to provide a current stress value stress of the person. For example, if the stress value is represented by using a hundred-mark system, the provided current stress value may be 75 marks. After performing the foregoing process, 100 pieces of sample information may be obtained. Each piece of sample information is corresponding to one person, and includes basic information, a one-minute ECG signal, and a subjectively provided stress value of the person.

For one piece of sample information, a heart rate HR and a standard deviation of the heart rate std_HR are calculated based on a one-minute ECG signal in the sample information, and a feature vector [Gender, Age, Height, Weight, HR, std_HR] is constructed by using the heart rate, the standard deviation of the heart rate, and the basic information in the sample information. A linear regression equation constructed based on the subjectively provided stress value in the sample and the feature vector corresponding to the sample information is $stress = a1 \times Gender + a2 \times Age + a3 \times Height + a4 \times Weight + a5 \times HR + a6 \times std\_HR + b$. A linear regression equation set formed by 100 linear regression equations may be obtained based on the 100 pieces of sample information, and regression coefficients a1, a2, a3, a4, a5, a6, and b of the linear regression equation set are obtained through calculation by using a least square method.

Therefore, the general stress model is $S = a1 \times Gender + a2 \times Age + a3 \times Height + a4 \times Weight + a5 \times HR + a6 \times std\_HR + b$, where a1, a2, a3, a4, a5, a6, and b are known, the gender, age, height, weight, HR, and std_HR are independent variables, and S is a stress value.

Optionally, before step 203, the method may further include: obtaining M physiological signals of the user in M time periods, where a physiological signal segment is a physiological signal of the user obtained in a time period, and M is an integer greater than 0; obtaining stress indicators that are subjectively provided by the user in M time periods, to obtain M subjective stress indicators, where the M subjective stress indicators are corresponding to the M time periods, respectively, and the M time periods are M time periods in which the M physiological signal segments are obtained; using the M physiological signal segments as input of a general stress model to obtain M general stress indicators; subtracting the M general stress indicators from the M subjective stress indicators to obtain M user offsets, where subtraction is performed between a subjective stress indicator and a general stress indicator that are corresponding to a same time period of the M time periods; and determining a sum of an average value of the M user offsets and a result of the general stress model as the instantaneous stress model.

Specifically, the bioelectric signal may be specifically an ECG signal and/or a PPG signal. The physiological signal is prone to be affected by an instantaneous factor, and therefore has relatively low reliability. However, the physiological signal may be collected by a device carried by the user, and therefore has relatively high portability. Therefore, the physiological signal may be used to determine the instantaneous stress model of the user, and improve accuracy of determining a stress indicator of the user.

It should be noted that, after the general stress model is obtained, because the general stress model is not a stress model of the user, the general stress model needs to be calibrated to obtain the instantaneous stress model of the user.

In addition to the physiological signal, the input of the general stress model includes another parameter, such as the age, height, and weight of the user that are mentioned in the foregoing embodiment. These parameters may be obtained from the user and pre-stored in a memory, for being invoked in calculating a general stress indicator.

Specifically, when the physiological signal is a PPG signal, stress indicators that are subjectively provided by the user in M two minutes may be obtained, to obtain M subjective stress indicators denoted as $Y_{11}, Y_{12}, \ldots, Y_{1M}$; PPG signals of the user in the M two minutes are collected as input of the general stress model, to obtain M general stress indicators denoted as $Y_{O1}, Y_{O2}, \ldots, Y_{OM}$; and M user offsets are $Y_{11}-Y_{O1}, Y_{12}-Y_{O2}, \ldots, Y_{1M}-Y_{OM}$. If the general stress model is denoted as Y_general, the instantaneous stress model of the user is Y_instant=Y_general+$[(Y_{11}-Y_{O1})+(Y_{12}-Y_{O2})+, \ldots, +(Y_{1M}-Y_{OM})]$/M.

Optionally, before step 203, the method may further include: obtaining a user offset, where the user offset is an offset, stored in another device and associated with the user, used to calibrate a general stress model; and determining a sum of the user offset and a result of the general stress model as the instantaneous stress model of the user.

Alternatively, the user offset may not be directly calculated based on the obtained M physiological signal segments and the M subjective stress indicators, but is obtained from another device (such as a server). For example, in one case, the user may create an account, and information such as the user offset and the age, height, and weight of the user is related to the account. The data may be stored in a server and is obtained when needed.

Figure 4:
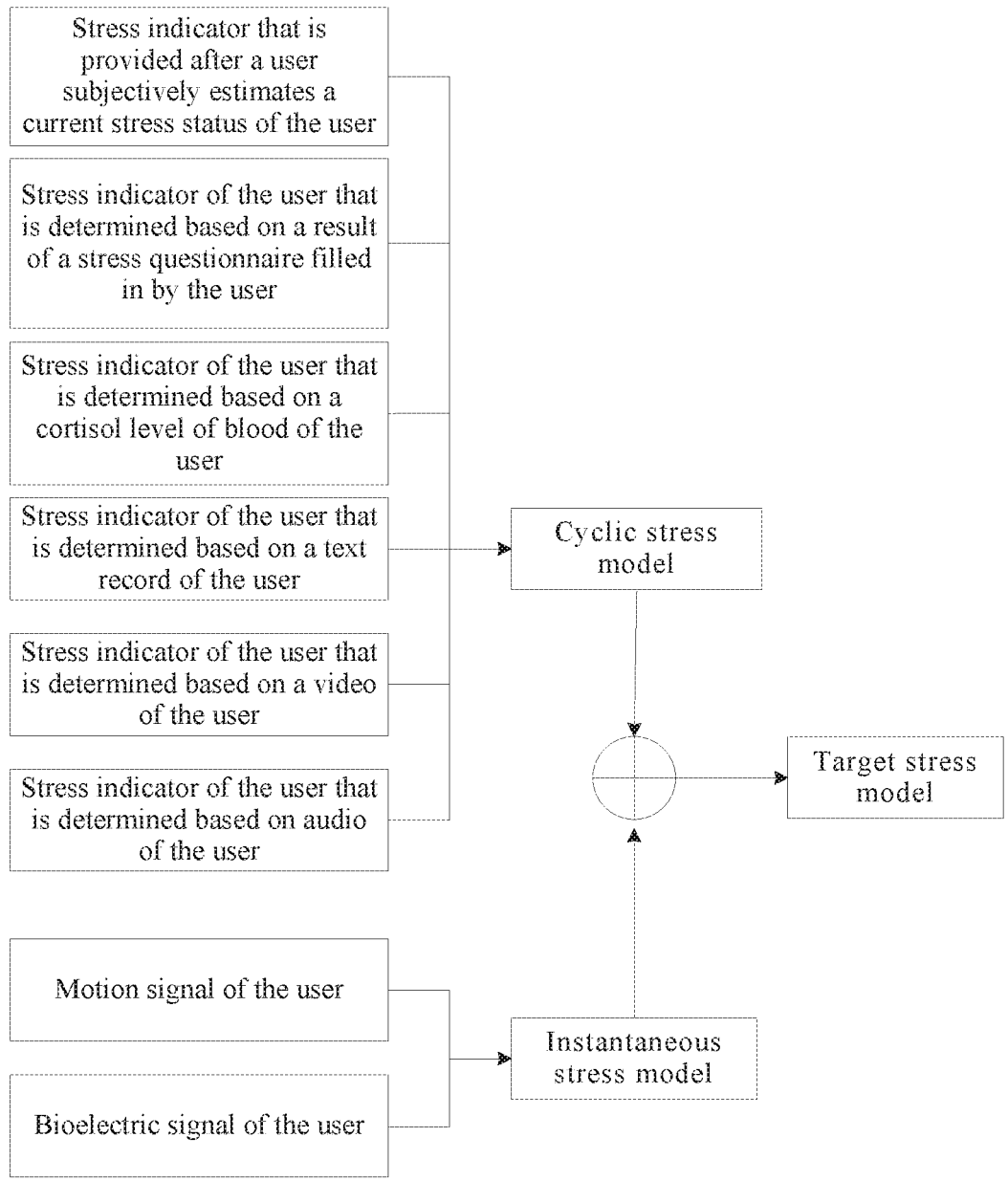
FIG. 4 is a schematic diagram of an overall process of determining a target stress model according to an embodiment of the present invention.

An example in which the target stress model is determined is used for description. As shown in FIG. 4, FIG. 4 shows an overall process of determining a target stress model. N discrete stress indicators are obtained based on at least one of a stress indicator provided by the user by subjectively estimating a current stress status of the user, a stress indicator of the user determined based on a result of a stress questionnaire filled in by the user, a stress indicator of the user determined based on a cortisol level of blood of the user, and a stress indicator of the user determined based on a text record, a video, or audio of the user; a cyclic stress model may be determined based on the N discrete stress indicators; M physiological signals of the user in M time periods are determined based on a motion signal and/or a bioelectric signal of the user; an instantaneous stress model may be determined based on the M physiological signal segments; and the target stress model is obtained by comprehensively processing the cyclic stress model and the instantaneous stress model.

It should be noted that, the cyclic stress model of the user is related only to time, but the instantaneous stress model of the user is related to the physiological signal and another parameter (such as an age, a height, and a weight of the user) of the user. Therefore, the target stress model is related to the time, the physiological signal, and the another parameter. In specific implementation, the another parameter of the user may be pre-stored in a memory of an apparatus for implementing the method provided in this embodiment of the present invention, and the time and the physiological signal may be obtained in real time by using a device carried by the user.

According to the method provided in this embodiment of the present invention, the preset time period may be one day, and in this case, the target stress model is a daily stress model of the user. By using the method, a target stress model for every day of one week may be obtained, and the target stress models for seven days of the week are combined to obtain a weekly stress model of the user. Certainly, the preset time period may alternatively be one week, and in this case, the target stress model is a weekly stress model of the user.

In a scenario, when the user needs to obtain a current stress indicator, the user may tap a button, disposed on the apparatus, for obtaining a physiological signal, to obtain an ECG signal of a time period (such as one minute or two minutes). The ECG signal implicitly includes a current moment.

The cyclic stress model may be a stress model that is obtained by performing curve fitting on discrete stress indicators or comprehensive discrete stress indicators. In this case, referring to FIG. 3, the cyclic stress model is a function in which time is an independent variable and a stress indicator is a dependent variable. A first stress indicator may be obtained by using the current moment as input of the cyclic stress model.

If the general stress model is S=a1×Gender+a2×Age+a3×Height+a4×Weight+a5×HR+a6×std_HR+b, and the user offset is c, the instantaneous stress model is S=a1×Gender+a2×Age+a3×Height+a4×Weight+a5×HR+a6×std_HR+b+c, where all of a1, a2, a3, a4, a5, a6, b, and c are known, the gender, age, height, and weight of the user may be obtained from a memory, HR and std_HR may be calculated based on the ECG signal, and the second stress indicator of the user may be calculated based on the ECG signal and the instantaneous stress model.

The current stress indicator of the user may be obtained by performing weighted summation on the first stress indicator and the second stress indicator.

According to the method provided in this embodiment of the present invention, a psychological stress of the user is qualitatively or quantatively estimated. This facilitates pushing of sport products and service products and auxiliary warning of a physical condition, can provide a warning when there is an excessive stress, and can facilitate arrangement of different things and work based on a daily psychological status, so as to improve life, work efficiency, or the like.

In addition, it should be noted that, the cyclic stress model and the instantaneous stress model (or the target stress model) may alternatively not be pre-stored in a device for implementing the method provided in this embodiment of the present invention, but is determined by the device after the device obtains a corresponding parameter that is used to determine the cyclic stress model and the instantaneous stress model (or the target stress model). After determining the cyclic stress model and the instantaneous stress model (or the target stress model), the device may store the cyclic stress model and the instantaneous stress model (or the target stress model) in the device.

It can be understood that, to implement the foregoing method, the apparatus configured to implement the foregoing method includes corresponding hardware structures and/or software units for performing the foregoing steps. A person skilled in the art should be easily aware that, in the present invention, units and algorithm steps in examples described with reference to the embodiments disclosed in this specification may be implemented by hardware or a combination of hardware and computer software. Whether a function is performed by hardware or by computer software driving hardware depends on particular applications and design constraint conditions of the technical solutions. A person skilled in the art may use a different method to implement the described functions for each particular application, but it should not be considered that the implementation goes beyond the scope of the present invention.

In the embodiments of the present invention, functional units of the apparatus configured to implement the foregoing method may be divided according to the foregoing examples of the method. For example, the functional units may be divided based on the functions, or two or more functional units may be integrated into one processing unit. It should be noted that, division of the functional units in the embodiments of the present invention is an example, and is merely logical function division and may be other division in actual implementation.

Figure 5:
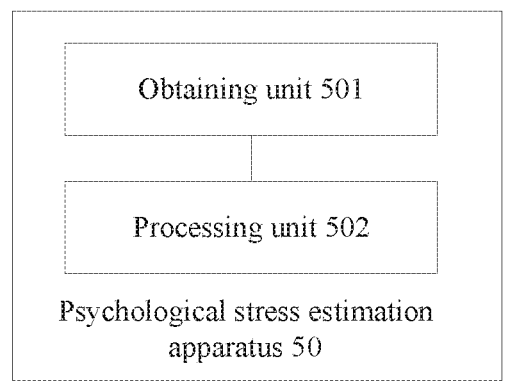
FIG. 5 is a schematic diagram of composition of a psychological stress estimation apparatus according to an embodiment of the present invention.

For example, as shown in FIG. 5, FIG. 5 shows a psychological stress estimation apparatus 50, including an obtaining unit 501 and a processing unit 502.

The obtaining unit 501 is configured to obtain a physiological signal of a user corresponding to a current moment.

The processing unit 502 is configured to determine a first stress indicator of the user based on the current moment and a cyclic stress model of the user, where the cyclic stress model is a stress model that is determined based on stress indicators of the user corresponding to a plurality of moments and that can be used to determine a current stress indicator of the user based only on the current moment.

The processing unit 502 is configured to determine a second stress indicator of the user based on the physiological signal of the user corresponding to the current moment and an instantaneous stress model of the user, where the instantaneous stress model is a stress model that is used to determine a current stress indicator of the user based on a physiological signal related to a current stress status of the user, and the physiological signal is input of the instantaneous stress model.

The processing unit 502 is configured to determine the current stress indicator of the user based on the first stress indicator and the second stress indicator.

Optionally, the cyclic stress model is a stress model that is determined based on at least one type of discrete stress indicator set, the discrete stress indicator set is a set of stress indicators that are determined based on discrete stress data that is obtained in a preset time period and is corresponding to at least one time point, and a discrete stress indicator in the discrete stress indicator set is a stress indicator that is determined based on a subjective estimation result of the user, a cortisol level of the user, or an external behavior of the user.

Optionally, the cyclic stress model includes a subjective cyclic stress model and an objective cyclic stress model; the subjective cyclic stress model is a stress model that is determined based on a type-1 discrete stress indicator set and/or a type-2 discrete stress indicator set, a discrete stress indicator in the type-1 discrete stress indicator set is a stress indicator that is determined based on a subjective estimation result of the user, and a discrete stress indicator in the type-2 discrete stress indicator set is a stress indicator that is determined based on an external behavior of the user; the objective cyclic stress model is a stress model that is determined based on a type-3 discrete stress indicator set, and a discrete stress indicator in the type-3 discrete stress indicator set is a stress indicator that is determined based on a cortisol level of the user; and the discrete stress indicator set is a set of stress indicators that are determined based on discrete stress data that is obtained in a preset time period and is corresponding to at least one time point.

Optionally, the cyclic stress model is a stress model that is determined based on a comprehensive discrete stress indicator set, the comprehensive discrete stress indicator set is a set of stress indicators that are determined based on at least one type of discrete stress indicator set, a comprehensive discrete stress indicator in the comprehensive discrete stress indicator set is determined based on a plurality of discrete stress indicators, the plurality of discrete stress indicators are all discrete stress indicators corresponding to a same time point in the at least one type of discrete stress indicator set, the discrete stress indicator set is a set of stress indicators that are determined based on discrete stress data that is obtained in a preset time period and is corresponding to at least one time point, and a discrete stress indicator in the discrete stress indicator set is a stress indicator that is determined based on a subjective estimation result of the user, a cortisol level of the user, or an external behavior of the user.

Optionally, the cyclic stress model is a stress model that is determined based on a comprehensive discrete stress indicator set and a plurality of historical discrete stress indicators, the comprehensive discrete stress indicator set is a set of stress indicators that are determined based on at least one type of discrete stress indicator set, a comprehensive discrete stress indicator in the comprehensive discrete stress indicator set is determined based on a plurality of discrete stress indicators, the plurality of discrete stress indicators are all discrete stress indicators corresponding to a same time point in the at least one type of discrete stress indicator set, the discrete stress indicator set is a set of stress indicators that are determined based on discrete stress data that is obtained in a preset time period and is corresponding to at least one time point, and a discrete stress indicator in the discrete stress indicator set is a stress indicator that is determined based on a subjective estimation result of the user, a cortisol level of the user, or an external behavior of the user; and the historical discrete stress indicator is a discrete stress indicator that is obtained before the preset time period.

Optionally, the obtaining unit 501 is further configured to: obtain M physiological signals of the user in M time periods, where a physiological signal segment is a physiological signal of the user obtained in a time period, and M is an integer greater than 0; obtain stress indicators that are subjectively provided by the user in M time periods, to obtain M subjective stress indicators, where the M subjective stress indicators are corresponding to the M time periods, respectively, and the M time periods are M time periods in which the M physiological signal segments are obtained.

The processing unit 502 is further configured to: use the M physiological signal segments as input of a general stress model to obtain M general stress indicators; subtract the M general stress indicators from the M subjective stress indicators to obtain M user offsets, where subtraction is performed between a subjective stress indicator and a general stress indicator that are corresponding to a same time period of the M time periods; and determine a sum of an average value of the M user offsets and a result of the general stress model as the instantaneous stress model.

Optionally, the obtaining unit 501 is further configured to obtain a user offset, where the user offset is an offset, stored in another device and associated with the user, used to calibrate a general stress model.

The processing unit 502 is further configured to determine a sum of the user offset and a result of the general stress model as the instantaneous stress model of the user.

Optionally, the physiological signal is a motion signal and/or a bioelectric signal.

The units of the apparatus 50 are configured to perform the method. Therefore, for beneficial effects of the apparatus 50, refer to beneficial effects of the method. Details are not repeated herein.

Figure 6:
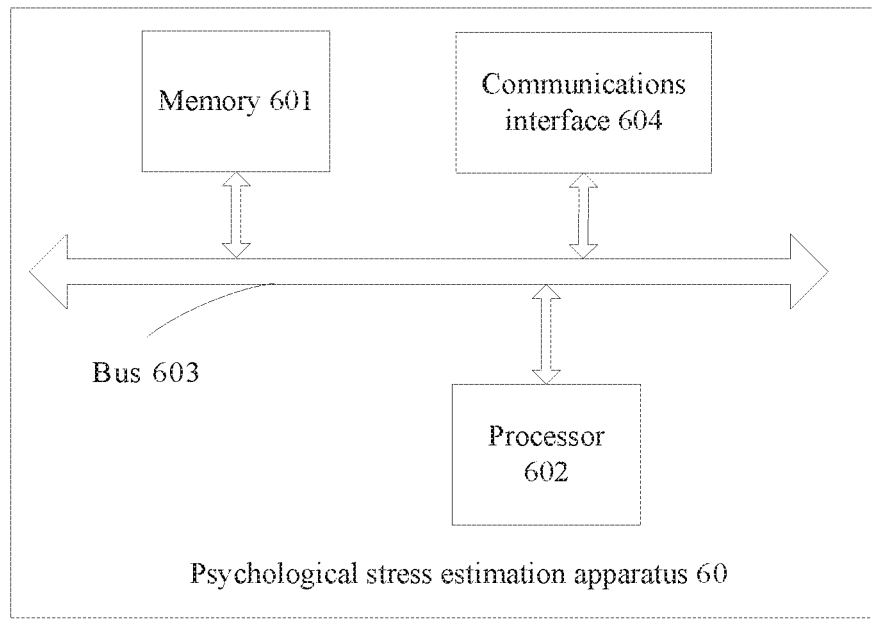
FIG. 6 is a schematic diagram of composition of another psychological stress estimation apparatus according to an embodiment of the present invention.

The operations performed by the units of the apparatus 50 may be executed by a processor of a psychological stress estimation apparatus, for example, may be executed by the processor 102 of the psychological stress estimation apparatus shown in FIG. 1. Compared with the psychological stress estimation apparatus shown in FIG. 1, a psychological stress estimation apparatus 60 shown in FIG. 6 is simpler. FIG. 6 shows a schematic structural diagram of hardware of the apparatus 60. The apparatus 60 includes a memory 601, a processor 602, a bus 603, and a communications interface 604. The memory 601 is configured to store a computer executable instruction, the processor 602 is connected to the memory 601 by using the bus 603, and the processor 602 executes the computer executable instruction stored in the memory 603, to implement the foregoing method.

For types of the memory 601 and the processor 602, refer to the related descriptions of the memory 101 and the processor 102. Details are not repeated herein.

The bus 603 may be a peripheral component interconnect (peripheral component interconnect, PCI) bus, an extended industry standard architecture (extended industry standard architecture, EISA) bus, or the like. The bus may be divided into address bus, a data bus, a control bus, and the like. For ease of indication, the bus is indicated by using only one bold line in FIG. 6. However, it does not indicate that there is only one bus or only one type of bus.

A person skilled in the art should be aware that in one or more of the foregoing examples, the functions described in the present invention may be implemented by using hardware, software, firmware, or any combination thereof. When this application is implemented by software, these functions may be stored in a computer-readable medium or transmitted as one or more instructions or code in the computer-readable medium. The computer-readable medium includes a computer storage medium and a communications medium, where the communications medium includes any medium that enables a computer program to be transmitted from one place to another. The storage medium may be any available medium accessible to a general or dedicated computer.

The objectives, technical solutions, and beneficial effects of the present invention are further described in detail in the foregoing specific embodiments. It should be understood that the foregoing descriptions are merely specific embodiments of the present invention, but are not intended to limit the protection scope of the present invention. Any modification, equivalent replacement, or improvement made based on the technical solutions of the present invention shall fall within the protection scope of the present invention.

What is claimed is:

1. A psychological stress estimation method, comprising:
    determining a cyclic stress model of a user based on a first set of stress indicators of the user corresponding to a plurality of moments;
    obtaining a first physiological signal of the user corresponding to a current moment;
    determining a first stress indicator of the user based on the current moment and the cyclic stress model;
    obtaining a user offset, wherein the user offset is an offset, stored in another device and associated with the user, calibrating a general stress model;
    setting a sum of an average value of the user offset and a result of the general stress model as an instantaneous stress model of the user, wherein the instantaneous stress model determines a current stress indicator of the user based on a second physiological signal related to a current stress status of the user, and wherein the second physiological signal is an input of the instantaneous stress model;
    determining a second stress indicator of the user based on the first physiological signal and the instantaneous stress model of the user; and
    determining the current stress indicator of the user based on the first stress indicator and the second stress indicator.

2. The psychological stress estimation method of claim 1, further comprising:
    obtaining, in a preset time period, discrete stress data corresponding to at least one time point;
    determining a discrete stress indicator set based on the discrete stress data;
    determining a discrete stress indicator comprised in the discrete stress indicator set based on a subjective estimation result of the user, a cortisol level of the user, or an external behavior of the user; and
    determining the cyclic stress model based on at least one type of discrete stress indicator set.

3. The psychological stress estimation method of claim 1, wherein the cyclic stress model comprises a subjective cyclic stress model and an objective cyclic stress model, and wherein the psychological stress estimation method further comprises:
    determining the subjective cyclic stress model based on a type-1 discrete stress indicator set or a type-2 discrete stress indicator set, wherein a first discrete stress indicator comprised in the type-1 discrete stress indicator set is based on a subjective estimation result of the user, and wherein a second discrete stress indicator comprised in the type-2 discrete stress indicator set is based on an external behavior of the user;

determining the objective cyclic stress model based on a type-3 discrete stress indicator set, wherein a third discrete stress indicator comprised in the type-3 discrete stress indicator set is based on a cortisol level of the user;

obtaining, in a preset time period, discrete stress data corresponding to at least one time point; and determining the discrete stress indicator set based on the discrete stress data.

4. The psychological stress estimation method of claim 1, further comprising:

obtaining, in a preset time period, discrete stress data corresponding to at least one time point;

determining a discrete stress indicator set based on the discrete stress data;

determining a discrete stress indicator comprised in the discrete stress indicator set based on a subjective estimation result of the user, a cortisol level of the user, or an external behavior of the user;

determining a comprehensive discrete stress indicator set based on at least one type of discrete stress indicator set;

determining the cyclic stress model based on the comprehensive discrete stress indicator set; and determining a comprehensive discrete stress indicator comprised in the comprehensive discrete stress indicator set based on a plurality of discrete stress indicators, wherein the discrete stress indicators are all discrete stress indicators corresponding to a same time point in the at least one type of discrete stress indicator set.

5. The psychological stress estimation method of claim 1, further comprising:

obtaining, in a preset time period, discrete stress data corresponding to at least one time point;

determining a discrete stress indicator set based on the discrete stress data;

determining a discrete stress indicator comprised in the discrete stress indicator set based on a subjective estimation result of the user, a cortisol level of the user, or an external behavior of the user;

obtaining a historical discrete stress indicator before the preset time period;

determining, based on at least one type of discrete stress indicator set, a comprehensive discrete stress indicator set;

determining the cyclic stress model based on the comprehensive discrete stress indicator set and a plurality of historical discrete stress indicators; and determining a comprehensive discrete stress indicator comprised in the comprehensive discrete stress indicator set based on a plurality of discrete stress indicators, wherein the discrete stress indicators correspond to a same time point in the at least one type of discrete stress indicator set.

6. The psychological stress estimation method of claim 1, wherein before determining the second stress indicator of the user, the psychological stress estimation method further comprises:

obtaining M physiological signals of the user in M time periods, wherein a physiological signal segment is a third physiological signal of the user obtained in a time period, and wherein M is an integer greater than zero;

obtaining a second set of stress indicators subjectively from the user in the M time periods to obtain M subjective stress indicators, wherein the M subjective stress indicators correspond to the M time periods, and wherein the M time periods are M time periods in which M physiological signal segments are obtained;

setting the M physiological signal segments as input of a general stress model to obtain M general stress indicators;

subtracting the M general stress indicators from the M subjective stress indicators to obtain M user offsets, wherein subtraction is performed between a subjective stress indicator and a general stress indicator corresponding to a same time period of the M time periods; and setting a sum of an average value of the M user offsets and a result of the general stress model as the instantaneous stress model.

7. The psychological stress estimation method of claim 1, wherein the first physiological signal and the second physiological signal are motion signals.

8. The psychological stress estimation method of claim 1, wherein the first physiological signal and the second physiological signal are bioelectric signals.

9. The psychological stress estimation method of claim 1, wherein the first physiological signal and the second physiological signal are motion signals and bioelectric signals.

10. A psychological stress estimation apparatus, comprising:

a memory configured to store instructions; and at least one processor coupled to the memory, wherein the instructions are executed by the at least one processor to cause the psychological stress estimation apparatus to be configured to:

determine a cyclic stress model of a user based on a first set of stress indicators of the user corresponding to a plurality of moments;

obtain a first physiological signal of the user corresponding to a current moment;

determine a first stress indicator of the user based on the current moment and the cyclic stress model of the user;

obtain a user offset, wherein the user offset is an offset, stored in another device and associated with the user, calibrating a general stress model;

set a sum of an average value of the user offset and a result of the general stress model as an instantaneous stress model of the user, wherein the instantaneous stress model determines a current stress indicator of the user based on a second physiological signal related to a current stress status of the user, and wherein the second physiological signal is an input of the instantaneous stress model;

determine a second stress indicator of the user based on the first physiological signal and the instantaneous stress model of the user; and determine the current stress indicator of the user based on the first stress indicator and the second stress indicator.

11. The psychological stress estimation apparatus of claim 10, wherein the instructions are further executed by the at least one processor to cause the psychological stress estimation apparatus to be configured to:

obtain, in a preset time period, discrete stress data corresponding to at least one time point;

determine a discrete stress indicator set based on the discrete stress data;

determine a discrete stress indicator comprised in the discrete stress indicator set based on a subjective estimation result of the user, a cortisol level of the user, or an external behavior of the user; and determine the cyclic stress model based on at least one type of discrete stress indicator set.

12. The psychological stress estimation apparatus of claim 10, wherein the cyclic stress model comprises a subjective cyclic stress model and an objective cyclic stress model, and wherein the instructions are further executed by the at least one processor to cause the psychological stress estimation apparatus to be configured to:

determine the subjective cyclic stress model based on a type-1 discrete stress indicator set or a type-2 discrete stress indicator set, wherein a first discrete stress indicator comprised in the type-1 discrete stress indicator set is based on a subjective estimation result of the user, and wherein a second discrete stress indicator comprised in the type-2 discrete stress indicator set is based on an external behavior of the user;

determine the objective cyclic stress model based on a type-3 discrete stress indicator set, wherein a third discrete stress indicator comprised in the type-3 discrete stress indicator set is based on a cortisol level of the user;

obtain, in a preset time period, discrete stress data corresponding to at least one time point; and determine the discrete stress indicator set based on the discrete stress data.

13. The psychological stress estimation apparatus of claim 10, wherein the instructions are further executed by the at least one processor to cause the psychological stress estimation apparatus to be configured to:

obtain, in a preset time period, discrete stress data corresponding to at least one time point;

determine a discrete stress indicator set based on the discrete stress data;

determine a discrete stress indicator comprised in the discrete stress indicator set based on a subjective estimation result of the user, a cortisol level of the user, or an external behavior of the user;

determine a comprehensive discrete stress indicator set based on at least one type of discrete stress indicator set;

determining the cyclic stress model based on the comprehensive discrete stress indicator set; and determine a comprehensive discrete stress indicator comprised in the comprehensive discrete stress indicator set based on a plurality of discrete stress indicators, wherein the discrete stress indicators are all discrete stress indicators corresponding to a same time point in the at least one type of discrete stress indicator set.

14. The psychological stress estimation apparatus of claim 10, wherein the instructions are further executed by the at least one processor to cause the psychological stress estimation apparatus to be configured to:

obtain, in a preset time period, discrete stress data corresponding to at least one time point;

determine a discrete stress indicator set based on the discrete stress data;

determine a discrete stress indicator comprised in the discrete stress indicator set based on a subjective estimation result of the user, a cortisol level of the user, or an external behavior of the user;

obtain a historical discrete stress indicator before the preset time period;

determine, based on at least one type of discrete stress indicator set, a comprehensive discrete stress indicator set;

determine the cyclic stress model based on the comprehensive discrete stress indicator set and a plurality of historical discrete stress indicators; and determine a comprehensive discrete stress indicator comprised in the comprehensive discrete stress indicator set based on a plurality of discrete stress indicators, wherein the discrete stress indicators correspond to a same time point in the at least one type of discrete stress indicator set.

15. The psychological stress estimation apparatus of claim 10, wherein the instructions are further executed by the at least one processor to cause the psychological stress estimation apparatus to be configured to:

obtain M physiological signals of the user in M time periods, wherein a physiological signal segment is a third physiological signal of the user obtained in a time period, and wherein M is an integer greater than zero;

obtain a second set of stress indicators subjectively from the user in the M time periods to obtain M subjective stress indicators, wherein the M subjective stress indicators correspond to the M time periods, and wherein the M time periods are M time periods in which M physiological signal segments are obtained;

set the M physiological signal segments as input of a general stress model to obtain M general stress indicators;

subtract the M general stress indicators from the M subjective stress indicators to obtain M user offsets, wherein subtraction is performed between a subjective stress indicator and a general stress indicator that are corresponding to a same time period of the M time periods; and set a sum of an average value of the M user offsets and a result of the general stress model as the instantaneous stress model.

16. The psychological stress estimation apparatus of claim 10, wherein the first physiological signal and the second physiological signal are motion signals and bioelectric signals.

17. The psychological stress estimation apparatus of claim 10, wherein the first physiological signal and the second physiological signal are motion signals or bioelectric signals.

18. A computer-readable storage medium having a program recorded thereon, wherein a computer executes the program to:

determine a cyclic stress model of a user based on stress indicators of the user corresponding to a plurality of moments;

obtain a first physiological signal of the user corresponding to a current moment;

determine a first stress indicator of the user based on the current moment and the cyclic stress model of the user;

obtain a user offset, wherein the user offset is an offset, stored in another device and associated with the user, calibrating a general stress model;

set a sum of an average value of the user offset and a result of the general stress model as an instantaneous stress model of the user, wherein the instantaneous stress model determines a current stress indicator of the user based on a second physiological signal related to a current stress status of the user, and wherein the second physiological signal is an input of the instantaneous stress model;
    determine a second stress indicator of the user based on the first physiological signal and the instantaneous stress model of the user; and
    determine the current stress indicator of the user based on the first stress indicator and the second stress indicator.

19. The computer-readable storage medium of claim 18, wherein the computer further executes the program to:
    obtain, in a preset time period, discrete stress data corresponding to at least one time point;
    determine a discrete stress indicator set based on the discrete stress data;
    determine a discrete stress indicator comprised in the discrete stress indicator set based on a subjective estimation result of the user, a cortisol level of the user, or an external behavior of the user; and
    determine the cyclic stress model based on at least one type of discrete stress indicator set.

20. The computer-readable storage medium of claim 18, wherein the cyclic stress model comprises a subjective cyclic stress model and an objective cyclic stress model, and wherein the computer further executes the program to:
    determine the subjective cyclic stress model based on a type-1 discrete stress indicator set or a type-2 discrete stress indicator set, wherein a first discrete stress indicator comprised in the type-1 discrete stress indicator set is based on a subjective estimation result of the user, and wherein a second discrete stress indicator comprised in the type-2 discrete stress indicator set is based on an external behavior of the user;
    determine the objective cyclic stress model based on a type-3 discrete stress indicator set, wherein a third discrete stress indicator comprised in the type-3 discrete stress indicator set is based on a cortisol level of the user;
    obtain, in a preset time period, discrete stress data corresponding to at least one time point; and
    determine the discrete stress indicator set based on the discrete stress data.

* * * * *